United States Patent [19]

Kajiyama et al.

[11] Patent Number: 4,531,663
[45] Date of Patent: Jul. 30, 1985

[54] GUIDE APPARATUS

[75] Inventors: Shigeru Kajiyama; Kazuo Takaku; Akisuke Naruse; Akira Akasu, all of Hitachi, Japan

[73] Assignees: Hitachi, Ltd., Tokyo; Hitachi Engineering Co., Ltd., Hitachi, both of Japan

[21] Appl. No.: 446,212

[22] Filed: Dec. 2, 1982

[30] Foreign Application Priority Data

Dec. 4, 1981 [JP] Japan ................. 56-194552

[51] Int. Cl.³ ............................................. B23K 5/08
[52] U.S. Cl. ...................................... 228/29; 104/118
[58] Field of Search ............ 104/118, 119; 238/10 R; 219/59.1, 60 A, 124.31, 159; 250/358.1; 378/59; 228/29, 49 B; 248/188.9

[56] References Cited

U.S. PATENT DOCUMENTS

| | | | |
|---|---|---|---|
| 3,196,245 | 7/1965 | Nelson et al. | 219/60 A |
| 3,266,700 | 8/1966 | Bauer et al. | 228/29 X |
| 3,890,482 | 6/1975 | DiBenedetto | 219/60 A X |
| 4,177,913 | 12/1979 | Iwamoto et al. | 219/60 A X |
| 4,336,436 | 6/1982 | Dubovetsky et al. | 219/60 A X |

FOREIGN PATENT DOCUMENTS

1592263  6/1970  France .................. 219/60 A

Primary Examiner—Randolph Reese
Attorney, Agent, or Firm—Beall Law Offices

[57] ABSTRACT

A guide apparatus comprises an annular rail and jaws for attaching the annular rail onto a cylindrical member to be inspected by an inspecting probe on the rail. The attaching jaws are provided on the rail and include at least two radially stationary jaws and at least one radially movable jaw. Each of the radially stationary jaws has a jaw surface to be abutted on an outer periphery of the cylindrical member. A radial distance between the abutting surface of the radially stationary jaw and the inner peripheral surface of the rail is discontinuously variable.

7 Claims, 17 Drawing Figures

GUIDE APPARATUS

BACKGROUND OF THE INVENTION

FIELD OF THE INVENTION

The present invention relates to a guide aparatus, and more particularly to a guide apparatus having rail means adapted to run a processing device along and over the outer peripheral surface of a cylindrical structure to be processed and to hold the same at predetermined positions over the outer peripheral surface of the structure. Still more particularly, the present invention is concerned with a guide apparatus suitable for use in examination of nozzles and pipes associated with a nuclear reactor.

DESCRIPTION OF THE PRIOR ART

In order to maintain nozzles or pipes associated with a nuclear reactor in good conditions, non-destructive inspection utilizing supersonic waves is conducted periodically to find out any defective part which is to be repaired or renewed without delay. In order to achieve a higher efficiency of the periodical inspection work, a remote control inspection system now has been in use in place of the conventional manual inspection system.

Generally speaking, for automatically conducting the non-destructive inspection utilizing supersonic waves on a member having a cylindrical surface, e.g. the aforementioned nozzle or pipe, the inspecting means is run by a driving means along an annular rail means coaxially arranged around the member to be inspected, so that the outer peripheral surface of the member is scanned along the axial direction and the circumferential direction by a probe of the inspecting means. The position of the defective portion requiring repair or renewal is precisely detected by means of the maintenance of a good reproducibility of the inspection, as well as good running conditions of the inspecting means.

A nuclear reactor has pipes and nozzles associated therewith of different diameters. In addition, nozzles or pipes of the same diameter are used on various portions of the nuclear reactor. In general, therefore, the annular rail means is designed to be mounted removably on such nozzle or pipe so as to remove it from the nozzle or pipe when the inspection is not made. The removable mounting of the annular rail means is also preferred for the reason that the permanent mounting of the rail means undesirably increases the outer diameter of the nozzle or pipe to waste a space because the nozzle or pipe is usually wrapped by a heat insulator.

Figure 1:
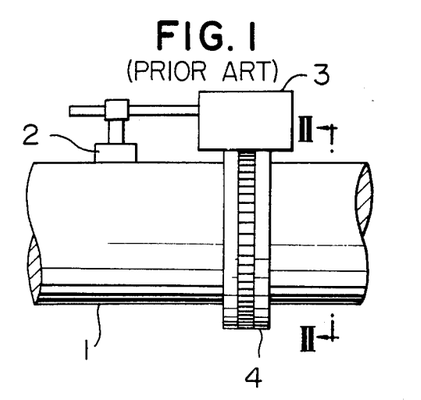
FIG. 1 is an illustration of a conventional guide apparatus attached to a pipe.
Figures 2, 3:
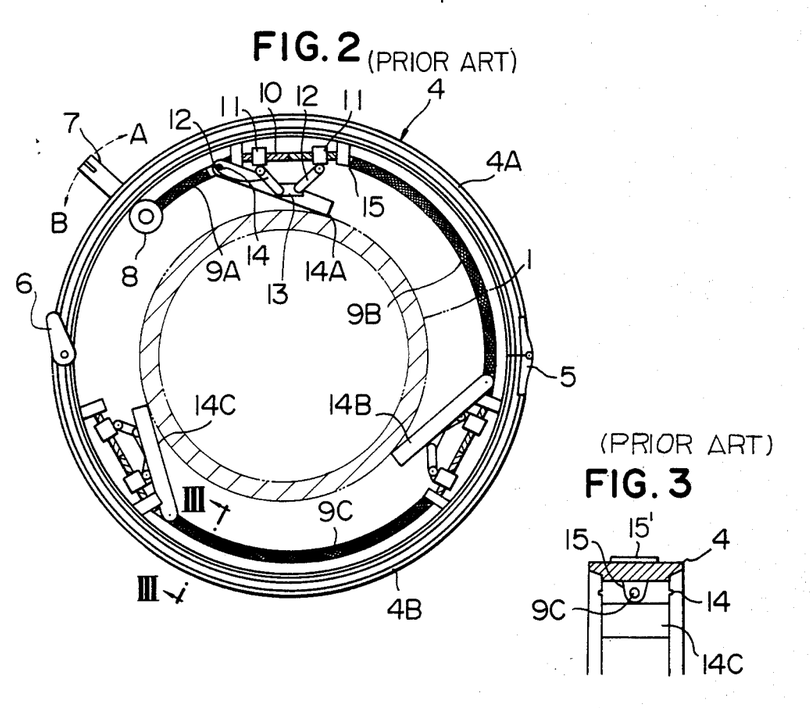
FIG. 2 is a sectional view taken along the line II—II of FIG. 1, without driving means.
FIG. 3 is a sectional view taken along the line III—III of FIG. 2.

FIGS. 1 to 3 show an example of the conventional guide apparatus. Referring first to FIG. 1, an annular rail means 4 coaxially mounted on a pipe 1 is provided with a driving means 3 for guiding and driving the inspecting means having a probe 2 to a portion of the pipe 1 to be inspected.

As roughly shown in FIGS. 2 and 3, the annular rail 4 is composed of two semi-circular rail halves 4A and 4B hinged by hinge 5 to each other at their one ends so that the other ends can be swung away from each other to provide a clearance for receiving the nozzle or pipe. For the detail of this annular rail, a refernce shall be made to Japanese Patent Laid-Open Publication No. 56-106150. The rails halves 4A and 4B in the swung away state are brought to close to the pipe 1 and are then locked by a lock handle 6 to complete a continuous annular rail 4. At the inner side of the annular rail, a flexible shaft having serial shaft pieces 9A to 9C is connected to an operating end of a manipulation handle 7 through a ratchet mechanism 8. The shaft pieces 9A to 9C are adapted to be rotated by the circumferential reciprocative operation of the handle 7, i.e. the movement in the directions of the arrows A and B. The rotation of the shaft piece 9A causes a rotation of a right and left screw 10 which is attached to the shaft piece 9A and which is provided with a right-threaded portion and left-threaded portion, so that movable elements 11 screw mounted on these threaded portions are moved on the screw 10 toward and away from each other. Arms 12 pivoted at their one ends to the movable elements 11 and a bar 13 pivoted at its opposite ends to the other ends of both arms 12 compose a link mechanism. The inclination angles of the arms 12 are changed as a result of the movement of the movable elements 11 to cause a movement of the bar 13. Consequently, a movable jaw 14A connected to the bar 13 is swung about a pivot 14 which is pivotally mounted on the shaft piece 9A, so that a free end of the movable jaw 14A is displaced toward the center of the annular rail. The rotation of the shaft piece 9A is transmitted to other shaft pieces 9B and 9C, so that other movable jaws 14B and 14C associated with these shaft pieces 9B and 9C are moved toward the center in the same manner. Thus, the annular rail 4 firmly clamps the outer peripheral surface of the corresponding pipe 1 through the movement of the movable jaws 14A to 14C. According to this arrangement, it is possible to absorb any fluctuation of the outer diameter of the pipe 1 through adjustment of stroke of movement of the movable jaws by a suitable control of operation of the handle 7. In these Figures, reference numerals 15 and 15' denote a bearing and a rack for running, respectively.

This conventional guide apparatus, however, has quite a complicated construction which in turn raises the production cost and increases the frequency of operation failure unfavorably. In addition, the guide apparatus of this type is adaptable only to pipes of a specific outer diameter and cannot be applied to pipes of various diameters. Namely, it has been necessary to prepare a plurality of rail means the number of which corresponds to that of various pipes of different diameters.

SUMMARY OF THE INVENTION

Accordingly, an object of the present invention is to provide a guide apparatus adaptable to various cylindrical structures having different outer diameters.

Meritorious features and advantages of the present invention will become clear from the following description of the preferred embodiments applied to the inspection of welded portion of a nuclear reactor pressure vessel, referring to the accompanying drawings.

DESCRIPTION OF THE PREFERRED EMBODIMENTS

Figure 4:
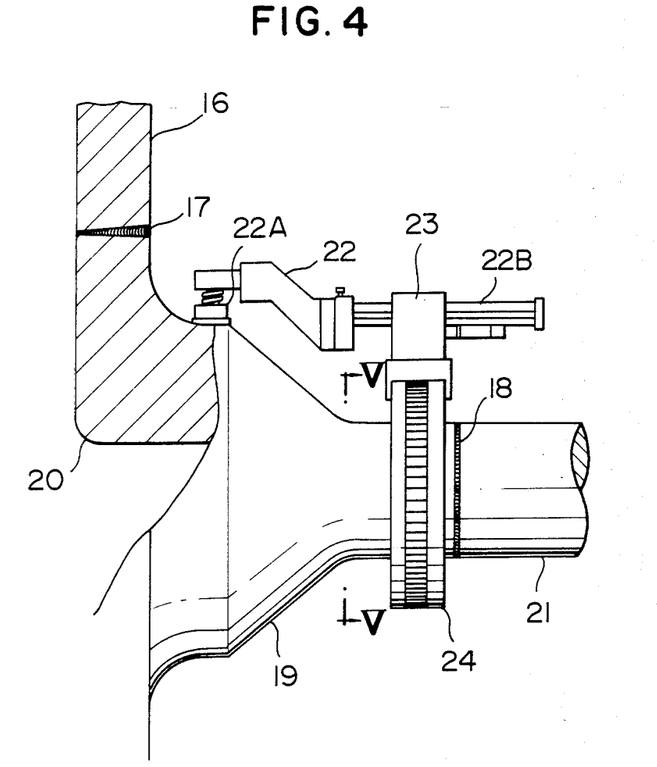
FIG. 4 is an illustration of an embodiment of the present invention attached to a nozzle.

In FIG. 4, a reducer nozzle 19 is connected at its one end to the opening of a pressure vessel 16 through a welded portion 17 while the other end of the nozzle is connected to a pipe 21 through another welded portion 18. Usually, the inner rounded annular edge portion 20 and welded portions 17 and 18 of the nozzle 19 are inspected by a probe 22A of a supersonic inspector 22. Through the inspection, an annular rail 24 is temporarily attached to an outer peripheral surface of the nozzle 10, and a driving means 23 is movably mounted on the annular rail 24 through a rack and pinion engagement. The driving means 23 is provided with the inspector 22 with the probe 22A. The probe 22A is adapted to be scanned around the outer peripheral surface of the nozzle 19 in both axial and circumferential directions, as a motor of the driving means 23 is operated in accordance with a command given by a control panel (not shown) through a cable. More specifically, the scanning in the axial direction is made through a guide 22B provided on the inspector 22.

Figure 5:
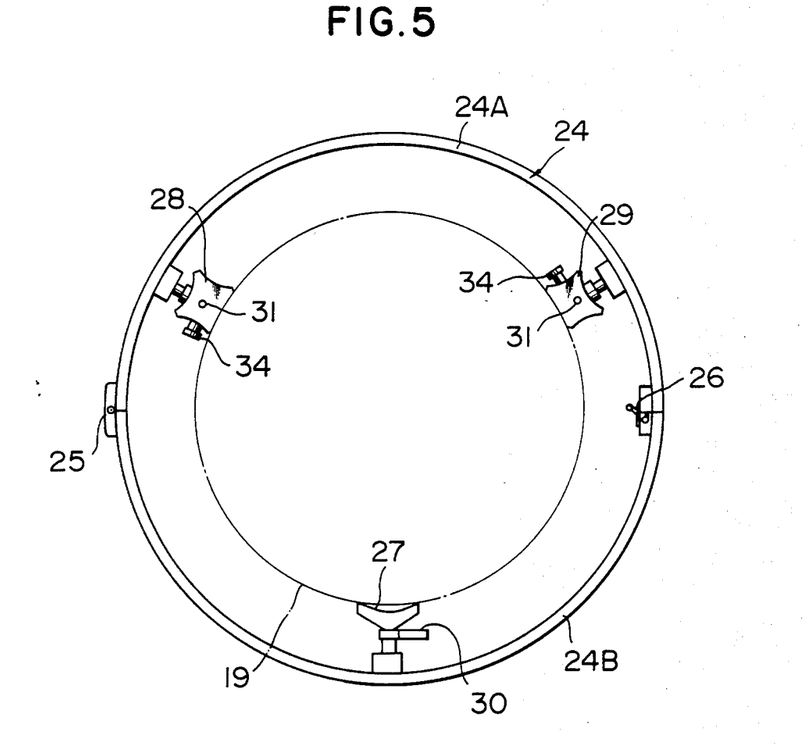
FIG. 5 is a sectional view taken along the line V—V of FIG. 4, without driving means.

As shown in FIG. 5, the annular rail 24 is composed of two semicircular halves 24A and 24B which are hinged at their one ends by hinge 25, so that the other ends are swingable away from each other to provide an access opening or to be locked in the closed state by the operation of a handle 26. Three jaw means 27, 28 and 29 are secured to the inner peripheral surface of the annular rail 24 at an equal circumferential pitch. More specifically, these jaw means are first jaw means 28 and 29 attached to one rail half 24A, a second jaw means 27 attached to the other rail half 24B.

As will be described later, the first jaw means 28 and 29 are adapted to rotate together with shafts 31 by the operation of push rods 34. The first jaw means is provided with rectangular jaw blocks. Each jaw block has four side walls which are curved at different radii of curvature. It will be understood that, since the end of the shaft 31 is connected to the jaw block at a portion thereof which is offset from the center of the jaw block, the radial distance between the inner peripheral surface of the rail 24 and the curved side wall of the jaw block to be contacted to the outer peripheral surface of the nozzle 19 can selectively take four different values at the jaw block is rotated together with the shaft 31. As will be explained later, the second jaw 27 is expandable and contractable in the radial direction.

In mounting the rail 24, the rail 24 in the opened state is brought close to the outer peripheral surface of the nozzle 19 to partly embrace the latter, and is then locked in the closed state by the operation of the handle 26. Then, the first jaw means 28 and 29 are suitably rotated to select such a radial distance as to position the rail 24 coaxially with the nozzle to be inspected. The radii of curvature of the curved side walls of the block and the amounts of offset of the curved side walls from the shaft 31 are so determined that the curved side walls make close contact with the outer peripheral surface of the nozzle to be inspected while two jaw means hold the rail 24 coaxially with the nozzle to be inspected. In this state, the second jaw 27 is extended radially inwardly to make the rail 24 securely clamp the nozzle 19.

Figure 6:
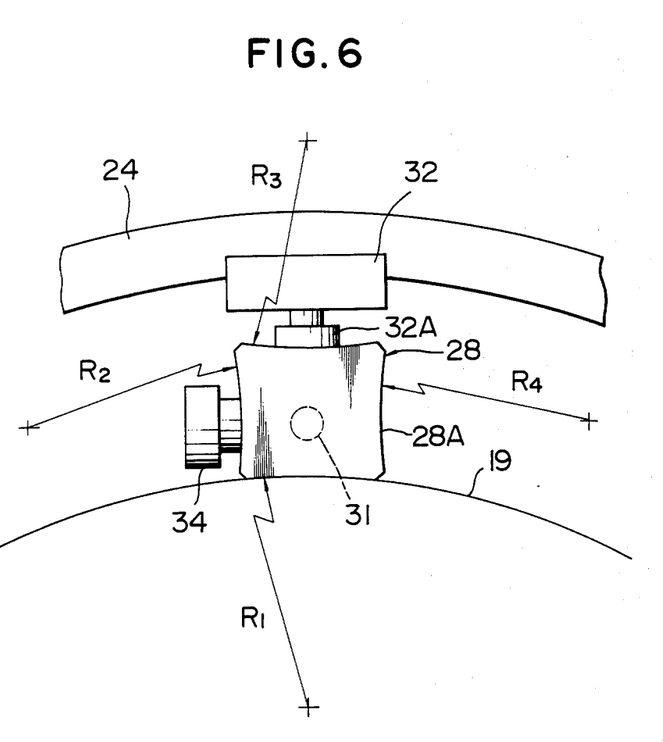
FIG. 6 is a plan view of a first jaw means incorporated in the embodiment shown in FIG. 4.
Figure 7A:
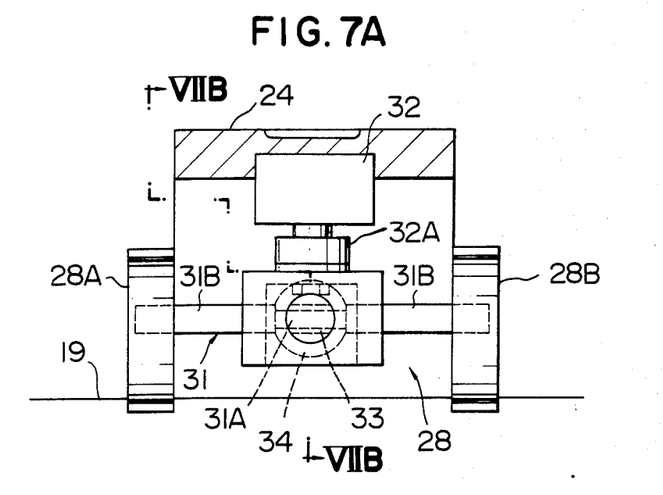
FIG. 7A is a side elevational view of the jaw means shown in FIG. 6.
Figure 7B:
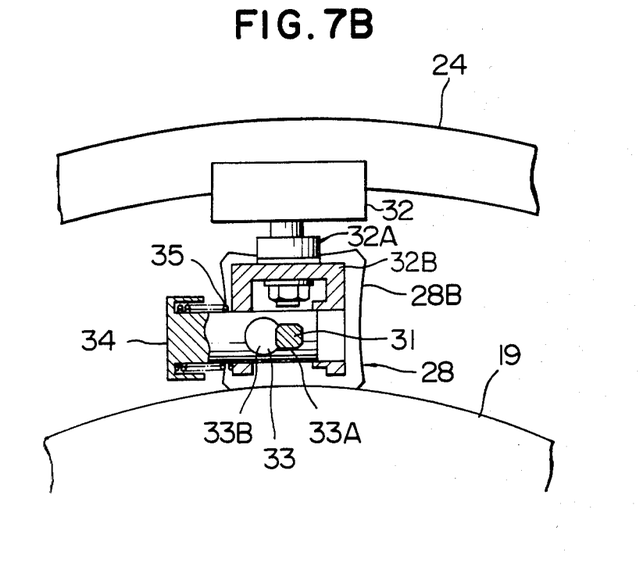
FIG. 7B is a sectional view taken along the line VIIB—VIIB in FIG. 7A.

A detailed description will be made hereinunder as to the construction and operation of the first jaw means 28 and 29, with specific reference to FIGS. 6 to 7B. The description, however, will be focussed mainly on the jaw means 28, because the jaw means 29 has an identical construction to the jaw means 28.

The jaw means 28 has a base 32 fixed to the inner peripheral surface of the annular rail 24, a rod 32A projecting radially inwardly from the base 32, and a channel bar 32B which is fixed at its bottom end to the end of the rod 32A. A capped push rod 34 movably extends through opposite walls of the channel bar 36. The capped push rod 34 is provided substantially at mid-portion thereof with a square bore 33A which extends radially through the push rod 34 and a circular bore 33B of a diameter greater than that of the square bore 33A. These two bores 33A and 33B partially overlapped each other to define a continuous large bore 33. A shaft 31 extends through the bore 33 in a direction perpendicular to the axis of the push rod 34, i.e. in parallel with the axis of the nozzle 19 to be inspected. A mid-portion 31A of the shaft 31 is provided with a square section closely engageable with the bore 33A and has an axial length substantially equal to the axial length of the wall of the channel bar 32B. A remainder portion 31B of the shaft 31 has a circular section of a diameter greater than that of the middle square. The outermost opposite ends of the shaft 31 are held at offset from the centers of jaw blocks 28A and 28B of the same structure. Each of these jaw blocks 28A and 28B is provided with four curved side walls of different radii of curvature represented by $R_1$, $R_2$, $R_3$ and $R_4$. The rod 34 is biased by a compression spring 35 which is disposed between one of the walls of the channel bar 32B and the cap of the push rod 34, so that the square bore section 33A and the middle square portion 31A of the shaft 31 are closely fitted each other to fix the jaw blocks 28A and 28B. When the blocks are required to rotate, the push rod 34 is pressed inwardly overcoming the biasing force of the spring 35, so that the square bore section 33A and the middle portion 31A of the shaft 31 are disengaged from each other to permit the middle portion 31A of the shaft 31 to rotate freely within the circular bore section 33B.

As the push rod 34 is relieved from the pressing force after the desired radius of curvature is selected by the rotation of the jaw blocks 28A and 28B together with the shaft 31, the push rod 34 is biased again by the biasing force of the spring 35, so that the middle portion 31A of the shaft 31 is brought again into close contact with the square bore section 33A thereby to fix the jaw blocks. The radius of curvature $R_i$ naturally coincides with the radius of curvature of the nozzle to be inspected and the amount of offset of the shaft 31 from the center of the jaw block is selected such that the center of the nozzle coincides with the center of the annular rail when the curved side wall of the jaw block is held in contact with the outer peripheral surface of the nozzle to be inspected. It will be understood that, by suitable selection of the curved side wall of the jaw block 28, it is possible to apply this rail apparatus to four kinds of nozzles having different outer diameters.

Figure 8A:
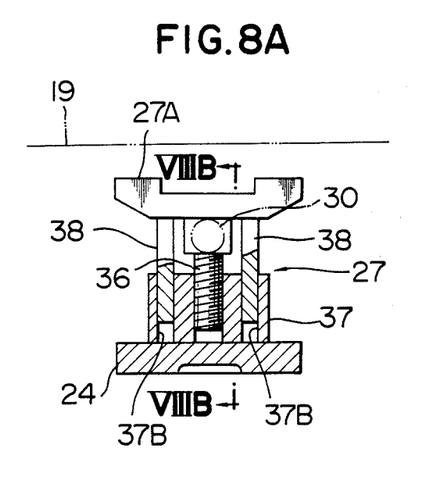
FIG. 8A is a detailed partial sectional view of the second jaw means incorporated in the embodiment shown in FIG. 4.
Figure 8B:
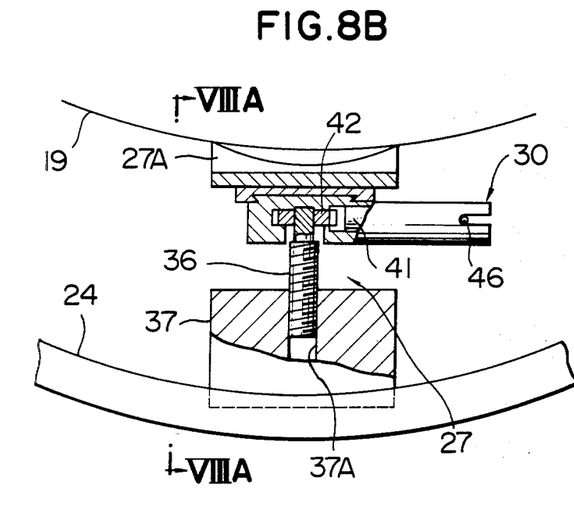
FIG. 8B is a sectional view taken along the line VIIIB—VIIIB in FIG. 8A.
Figures 9, 10, 11A:
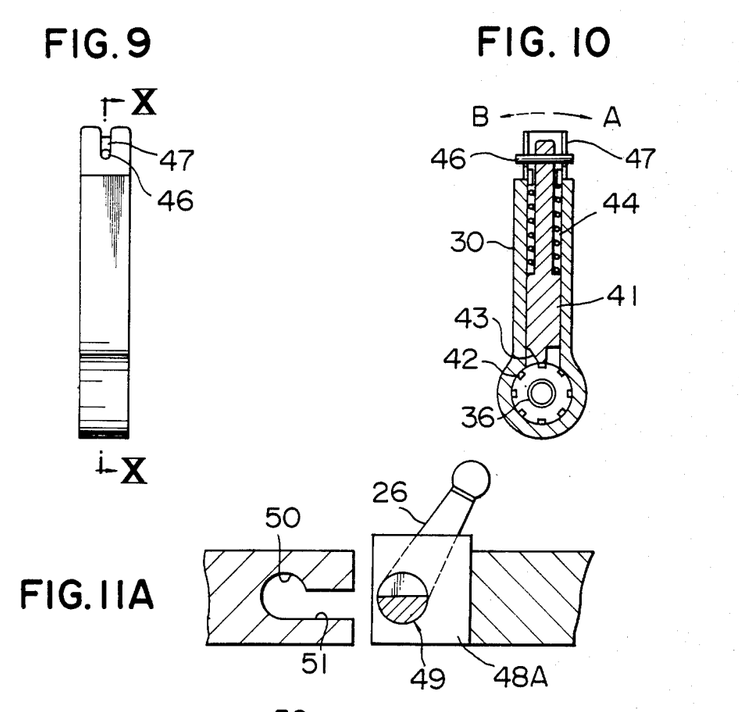
FIG. 9 is a side elevational view of a handle shown in FIG. 8B.
FIG. 10 is a sectional view taken along the line X—X in FIG. 9.
FIG. 11A is a sectional view of a handle portion shown in FIG. 5 taken along the line XIA—XIA in FIG. 11B.

A description will be made hereinunder as to the construction and operation of the second jaw means 27 with specific reference to FIGS. 8A to 10. The detail of such means is disclosed in Japanese Patent Laid-Open Publication No. 56-106150. The jaw means 27 has a base 37 which is fixed to the inner peripheral surface of the annular rail 24 and provided therein with a radially extending threaded bore 37A, and a jaw 27A provided with a ratchet handle 30. As shown in FIGS. 9 and 10, the ratchet handle 30 has a casing, a ratchet 42 rotatably housed in the casing and provided on its peripheral surface with a circumferential recess row, a rod 41 having a pawl engageable with the recess, and a spring 44 adapted to bias the rod. The jaw means 27 further has a threaded shaft 36 fixed at its end to the ratchet 42 and screw engageable with the threaded bore 37A in the base 37.

The operation of the jaw means 27 is as follows. As circumferential reciprocal motion in the directions of arrows A and B in FIG. 10 is imparted to the handle 30, the ratchet 42 is rotated only in one direction (arrow A) because one side 43 of the pawl is tapered so as to avoid the engagement between the recess and the pawl. The rotation of the ratchet 42 in turn causes a rotation of the threaded shaft 36, so that the jaw 27 is extended radially inwardly to contact the outer peripheral surface of the nozzle 19. For retracting the jaw 27 radially outwardly to disengage the nozzle 19, the pin 46 extending through a slot 47 in the handle 30 and a bore formed in the end portion of the rod 41 opposing to the pawl is grasped. The pin 46 and rod 41 are withdrawn from the slot 47 against the bias of spring 44, rotated 180° and inserted in the slot to reverse the tapered side 43 of the pawl. In this state, the ratchet 42 becomes rotatable only in the opposite direction (arrow B), so that the threaded shaft 36 is rotated in the reverse direction together with the ratchet 42 to retract the jaw 27 radially outwardly thereby to disengage the jaw 27 from the nozzle 19. In FIG. 8A, two stays 38 prevent rotation of the jaw 27. Each stay 38 is fixed at its one end of the jaw 27 while the other end is slidably received in a guide bore 37B formed in the base 37.

Figures 11B, 11C:
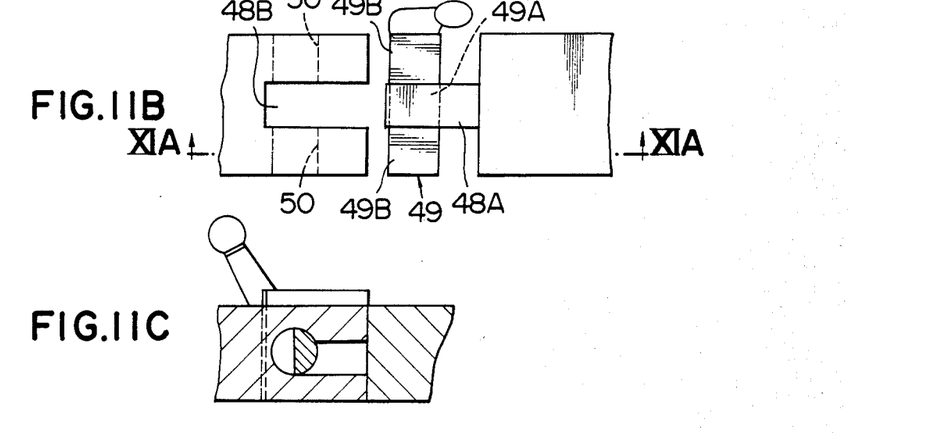
FIG. 11B is a plan view of the handle portion shown in FIG. 11A.
FIG. 11C is a sectional view showing the handle portion in the locked state.

An explanation will be made hereinunder as to a construction of the ends of the rail halves 24A and 24B for opening and closing the annular rail 24. The detail of this construction is disclosed in Japanese Patent Laid-Open Publication No. 56-47756. A connection between the ends of the rail halves is made in a forked mortise and tenon joint fashion. More specifically, a shaft 49 is rotatably attached to a tenon portion 48A provided on one end of one rail half. A portion 49A of the shaft 49 surrounded by the tenon portion 48A has a circular cross-section while other portion 49B of the shaft 49 has a semicircular cross-section. A handle 26 for rotating the shaft 49 is provided at one end of the latter. A mortise portion 48B provided on one end of the other rail half has coaxial bores 50 of a diameter substantially equal to the outer diameter of the shaft 49 and slots 51 having a width slightly smaller than the diameter of the bore 50 and extending from the end surface of the mortise portion to the bore 50. For connecting the rail halves, the tenon portion 48A is pressed into the bottom of the mortise portion 48B and the handle is swung to rotate the semicircular cross-sectioned portion 49B in a 90° arc, thereby to lock these rail halves. The shaft 49 is never dropped out from the bores 50 because the slot 51 has a width somewhat smaller than the outer diameter of the shaft 49.

As will be understood from the foregoing description, the mechanism of attaching the rail to the outer peripheral surface of the nozzle is very much simplified as compared with the conventional guide apparatus. Accordingly, such simplified construction offers various advantages such as reduction of the production cost due to a reduction in number of parts, improvement in the reliability due to a reduction in the frequency of trouble. The guide apparatus of the described embodiment will fully exhibit its advantages when applied to structures having peripheral surfaces machined highly precisely to avoid any substantial dimensional error.

Furthermore, according to the described embodiment of the present invention it is possible to freely select four different radial distances between the inner peripheral surface of the annular rail and the surface of the jaw adapted to contact with the structure to be inspected by a simple operation. This means that a single guide apparatus of the present invention can be used for four kinds of structures having different diameters. This in turn permits the user to reduce the number of guide apparatus to be used for different structures of a variety of outer diameters advantageously.

It is to be noted also that the guide apparatus of the described embodiment can be operated without requiring any specific skill or experience, and can be mounted and demounted within a shorter time than the conventional apparatus. This offers a specific advantage of reduction in the radiation exposure of the workers, particularly when the guide apparatus is applied to the inspection of internal structures of a nuclear power generating plant or the like.

Although in the described embodiment two first jaw means 28 and 29 and one second jaw means 27 are used in combination, these numbers of the jaw means are not exclusive. The number of the side walls of each jaw of the first jaw means may be changed owing to the demand for various sizes of structures to be inspected, although in the described embodiment the jaw of the first jaw means has four curved side walls thereby to cope with four different sizes of the structure.

Thus, the present invention is not limited to the described embodiment solely, but can be embodied in different ways as will be explained hereinunder. In the following description of other embodiments, the same reference numerals are used to denote the same parts or members as those used in the first embodiment described hereinbefore.

Figure 12:
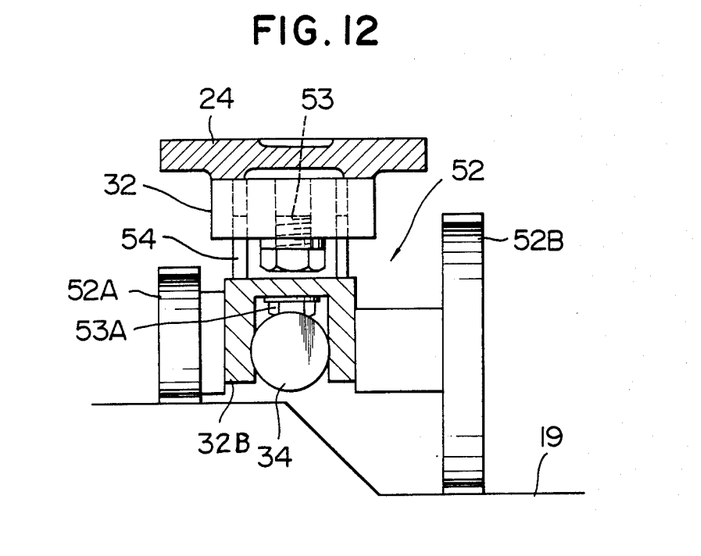
FIG. 12 is a sectional view of a first jaw means incorporated in another embodiment.

In an embodiment shown in FIG. 12, the first jaw means 52 has jaws 52A and 52B the sizes of which are not identical and differed in the radial direction so as to permit the attaching of the annular rail 24 to the stepped portion of the member 19. The engagement between the stepped portion of the member 19 and the jaw means 52 can be adjustable not only by the rotations of the jaws 52A and 52B but also by the radial displacement of a cap bolt 53 caused by a rotation of a nut 53A. This adjustement can be applied also to the first embodiment explained before. A reference numeral 54 designates a guide stay.

Figure 13:
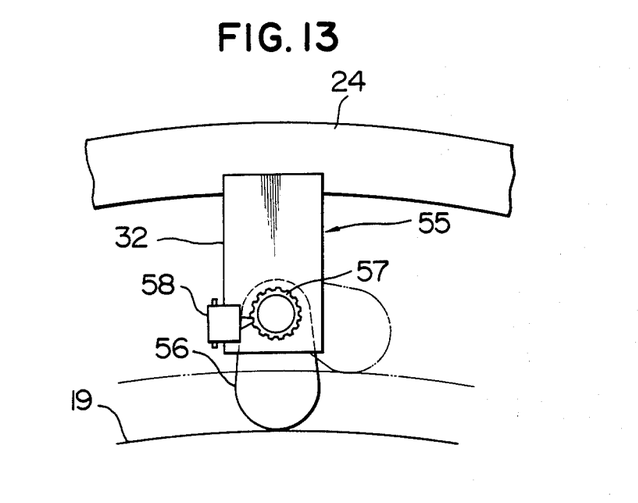
FIG. 13 is a sectional view of a first jaw means incorporated in still another embodiment.

In still another embodiment shown in FIG. 13, the first jaw means 55 incorporates a ratchet gearing system. A tongue-like jaw 56 is adjustable to follow a change of the outer diameter of the structure to be inspected by the combination of a rotatable ratchet 57 fixed to the jaw 56 and a pawl means 58 engageable with the ratchet 57.

It is also possible to use a ratchet having a discontinuous tooth row in place of the illustrated continuous tooth row, to make the guide apparatus applicable only to structures having specific outer diameters.

In the described embodiment, handle-operated ratchet drive mechanism is used for causing the radial displacement of the jaw of the second jaw means. This, however, is not exclusive and it is possible to use a hydraulic or pneumatic cylinder-piston driving mechanism or a motor drive system in place of the ratchet driving mechanism.

Although the present invention has been described through specific embodiments applied to the inspection of nozzle and pipe, it will be clear to those skilled in the art that the guide apparatus of the present invention can be used for various other purposes such as guiding of an automatic welding means for welding various cylindrical structures.

As has been described, the present invention provides a guide apparatus having a simplified construction and applicable to a variety of sizes of structures.

What is claimed is:

1. A guide apparatus comprising:
an annular rail means adapted to be attached concentrically to an outer periphery of a cylindrical member to be processed by a processing means;
attaching means provided on an inner peripheral surface of said annular rail means for attaching said annular rail means onto the outer periphery of said cylindrical member;
driving means for running said processing means along above the outer periphery of said cylindrical member;
wherein said attaching means includes at least two first jaw means each having a jaw surface to be abutted on a part of the outer periphery of said cylindrical member and at least one second radially movable jaw means for stationarily clamping said annular rail means onto said cylindrical member, said first jaw means are disposed on said annular rail means so as to concentrate a center of said annular rail means on that of said cylindrical member, and wherein a radial distance between said abutting surface of said first jaw means and the inner peripheral surface of said annular rail means is discontinuously variable; and
said first jaw means comprises polygonal jaw blocks at least two side walls of each block having curved surfaces the radii of curvature of which correspond to that of the cylindrical member to be processed, and wherein each said block is rotatable about a shaft fixed against said annular rail means and distances between said curved surfaces of each said block and the axis of each said shaft differ from one another.

2. A guide apparatus as claimed in claim 1, wherein said annular rail means is divided into two rail sections, and wherein all of said first jaw means are provided on one of said rail sections.

3. A guide apparatus as claimed in claim 1 or 2, wherein said processing means comprises welding means and/or inspecting means for inspecting a portion of said cylindrical member which is welded by said welding means.

4. A guide apparatus as claimed in claim 3, wherein said shaft has a noncircular portion and said rail means has an aperture with a first noncircular portion of mating configuration with said shaft noncircular portion to prevent relative rotation therebetween and an immediately adjacent enlarged aperture portion permitting free rotation of said shaft when said noncircular portion is therein; indexing means, including said noncircular portions and said aperture portions providing for relative movement between said shaft and said aperture for indexing said shaft while in said enlarged aperture portion to change the jaw surface facing the cylindrical member and lock the shaft against rotation in the indexed position wherein said noncircular portions are mating, and resilient means biasing said shaft and aperture toward mating engagement of said noncircular portions.

5. A guide apparatus as claimed in claim 4, wherein said shaft is mounted with an axis of rotation parallel to the annular rail means; said indexing means being a push rod mounted on said rail means for sliding movement transverse to said shaft, and said push rod having therein said aperture; and said resilient means being a spring mounted between said push rod and said rail means.

6. A guide apparatus as claimed in claim 1 or 2, wherein said shaft has a noncircular portion and said rail means has an aperture with a first noncircular portion of mating configuration with said shaft noncircular portion to prevent relative rotation therebetween and an immediately adjacent enlarged aperture portion permitting free rotation of said shaft when said noncircular portion is therein; indexing means, including said noncircular portions and said aperture portions providing for relative movement between said shaft and said aperture for indexing said shaft while in said enlarged aperture portion to change the jaw surface facing the cylindrical member and lock the shaft against rotation in the indexed position wherein said noncircular portions are mating, and resilient means biasing said shaft and aperture toward mating engagement of said noncircular portions.

7. A guide apparatus as claimed in claim 6, wherein said shaft is mounted with an axis of rotation parallel to the annular rail means; said indexing means being a push rod mounted on said rail means for sliding movement transverse to said shaft, and said push rod having therein said aperture; and said resilient means being a spring mounted between said push rod and said rail means.

* * * * *